(12) United States Patent
Kim et al.

(10) Patent No.: US 6,878,409 B2
(45) Date of Patent: Apr. 12, 2005

(54) METHOD FOR PRODUCING SILVER SALT-CONTAINING FACILITATED TRANSPORT MEMBRANE FOR OLEFIN SEPARATION HAVING IMPROVED STABILITY

(75) Inventors: Hoon Sik Kim, Seoul (KR); Yong Soo Kang, Seoul (KR); Byung Gwon Lee, Seoul (KR); Hyun Joo Lee, Seoul (KR); Jae Hee Ryu, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 10/773,257

(22) Filed: Feb. 9, 2004

(65) Prior Publication Data
US 2004/0154980 A1 Aug. 12, 2004

Related U.S. Application Data

(62) Division of application No. 10/194,303, filed on Jul. 15, 2002, now Pat. No. 6,706,771.

(30) Foreign Application Priority Data

Jul. 16, 2001 (KR) ........................................ 2001-42699

(51) Int. Cl.$^7$ ................................................ B05D 3/02
(52) U.S. Cl. ........................ 427/372.2; 521/27; 521/31; 210/638; 210/651; 427/384; 427/385.5
(58) Field of Search ..................... 521/27, 31; 210/638, 210/651; 427/372.2, 384, 385.5

(56) References Cited

U.S. PATENT DOCUMENTS

| | | | |
|---|---|---|---|
| 3,758,603 A | | 9/1973 | Steigelmann et al. ....... 260/677 |
| 4,891,125 A | * | 1/1990 | Schultz ...................... 204/435 |
| 5,015,268 A | | 5/1991 | Ho ............................... 55/16 |
| 5,152,899 A | * | 10/1992 | Berger et al. ............... 210/644 |
| 5,236,570 A | * | 8/1993 | Ma et al. .................. 204/403.06 |
| 5,670,051 A | | 9/1997 | Pinnau et al. .............. 210/651 |

OTHER PUBLICATIONS

Safarik et al., "Olefin/Paraffin Separations by Reactive Absorption: A Review", Ind. Eng. Chem. Res. vol. 37, No. 7, pp. 2571–2581 (1998).
Jose et al., Chemical Communications (2001), (20), pp. 2046–2047.
Jose et al., Chemistry of Materials (2002), 14(5), pp. 2134–2139.

* cited by examiner

Primary Examiner—Helen L. Pezzuto
(74) Attorney, Agent, or Firm—Finnegan, Henderson, Farabow, Garrett & Dunner, LLP

(57) ABSTRACT

The present invention relates to polymer membranes for separating olefins from paraffins which have the similar molecular size and close boiling point. More particularly, it relates to a silver salt-containing facilitated transport membrane for olefin separation, and also a method for producing the same. An object of the present invention is to provide a silver salt-containing facilitated transport membrane for olefin separation having improved stability, and also a method for preparing the same, which exhibits no deterioration in membrane performance even when operated for an extended period of time. The facilitated transport membrane for olefin/paraffin separation of the present invention comprises a polymer, a silver salt, and a phthalate compound represented by the following formula (1)

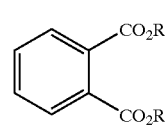

(1)

wherein R denotes an alkyl group of 2 to 8 carbon atoms or a phenyl group.

4 Claims, No Drawings

METHOD FOR PRODUCING SILVER SALT-CONTAINING FACILITATED TRANSPORT MEMBRANE FOR OLEFIN SEPARATION HAVING IMPROVED STABILITY

This is a division of application Ser. No. 10/194,303, filed Jul. 15, 2002 now U.S. Pat. No. 6,706,771, which is incorporated herein by reference.

BACKGROUND OF THE INVENTION

1. Field of the Invention

The present invention relates to facilitated transport membranes for olefin/paraffin separation, and more particularly to silver-containing polymer membranes with improved stability for olefin/paraffin separation and a method for preparing the same.

2. Description of the Prior Art

Olefins, basic raw materials for the chemical industry, are mainly obtained by cracking naphtha or natural gas as mixtures with saturated hydrocarbons with close volatilities, and thus olefins must be separated before they can be used.

Currently, separation of olefin/paraffin mixture is mainly carried out by highly energy-intensive low temperature distillation. As a result, a number of alternatives have been investigated including adsorption and membrane separation.

There was reported a method for separating olefins from paraffins by adsorption using silver or copper salts which reversibly react with olefins (see, *Ind. Eng. Chem. Res.* 2571 (1998)). However, this separation method using adsorption is disadvantageous because desorption process must be carried out after adsorption, thereby requiring a large equipment and space.

Recently, separation by facilitated transport membranes in which silver salts are used as carriers has attracted much interest because of the low energy consumption, compact apparatus, and simple operation. The basis for the separation is the ability of silver ions to interact reversibly with olefins by forming silver-olefin complexes. There have been many reports on the facilitated transport of olefins by using various membranes such as supported liquid membranes and ion-exchange membranes; however those membranes, as disclosed in U.S. Pat. No. 3,758,603, exhibit high olefin/paraffin selectivity only in the presence of water, requiring costly and undesirable humidification and dehumidification steps in the practical applications.

A solution to this problem is the development of facilitated transport polymer membranes. U.S. Pat. No. 5,670,051 discloses a facilitated transport polymer membrane in which silver salt present in polymer matrix interacts with olefins. According to this patent, separation of olefins from paraffins is conducted in the absence of water, so that loss of the silver salt caused by introduction of gas does not occur. Furthermore, since the polymer membrane can be produced so as to have a reduced thickness of several $\mu$m or below, gas permeability can be significantly increased. In addition, much larger amounts of silver salts can be used in comparison with other types of membranes, and thus the separation efficiency can be significantly increased.

However, polymer membranes containing silver salts exhibit some disadvantages that prevent the commercialization of this separation process. One major drawback observed in the polymer membrane is the decrease in membrane performance with time, possibly due to the reduction of silver ions to silver particles by light or impurities.

SUMMARY OF THE INVENTION

Accordingly, the present invention has been made to solve the above-mentioned problems occurring in the prior art, and an object of the present invention is to provide a silver salt-containing facilitated transport membrane for olefin separation having improved stability and also a method for producing the same, which exhibits no deterioration in membrane performance even when it is operated for an extended period of time.

To accomplish this object, there is provided a facilitated transport membrane for olefin/paraffin separation, which comprises a polymer, a silver salt, and a phthalate compound represented by the following formula (1):

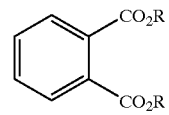

(1)

wherein R denotes an alkyl group of 2 to 8 carbon atoms or a phenyl group.

DETAILED DESCRIPTION OF THE PREFERRED EMBODIMENTS

In the facilitated transport polymer membranes according to the present invention, phthalates are able to bind to silver ions in a chelating mode, thereby improving the stability and performance of the membranes.

The membranes in the present invention comprise polymer matrix as solvent and a silver salt capable of reversibly interacting with olefins as transport carrier and solute.

The material chosen for the polymers should promote dissolution of the silver salt into the polymer matrix, and provide high mobility for complexed olefin molecules.

Based on these factors, preferred polymers are those that can form coordination bonds to silver ions by means of oxygen, nitrogen or sulfur electron-donating atom, known as a hetero-atom, in the polymer structure.

In other words, the polymer is used, which has a functional group, such as amide, ether, ester or carbonylic acid. Examples of this polymer include polyvinylpyrrolidone (PVP), poly(2-ethyl-2-oxazoline), polyvinylmethylketone, polyvinylformal, polyvinylacetate, cellulose acetate (CA), cellulose acetate butyrate (CAB), polyacrylate, polymethylmethacrylate (PMMA), polyacrylic acid and the like.

In the polymer membranes according to the present invention, the molar ratio of silver salt/monomer unit of polymer ranges from 0.5–3, and preferably 1–2. Examples of the silver salt, which can be used in the practice of the present invention, include $AgBF_4$, $AgPF_6$, $AgSO_3CF_3$, $AgClO_4$, $AgSbF_6$ and the like. In addition, other silver salts, which can chemically bind to the functional group of the polymer, may also be used.

The phthalate compound is contained at the amount of 0.05 to 10% by weight, and preferably 1 to 5 % by weight, relative to the weight of the polymer. If the phthalate compound content is below 0.05% by weight, it is disadvantageous in that an improvement of performance and stability of the separation membrane is insufficient. On the other hand, if the phthalate content exceeds 10% by weight, it is also disadvantageous in that the permeance of olefins is significantly reduced.

Furthermore, the facilitated transport membrane for olefin/paraffin separation is produced by a method which comprises the steps of: successively dissolving a polymer, a silver salt and a phthalate compound in a solvent to form a homogeneous solution; coating the solution on a support; and drying the coated support at a condition free of light and oxygen.

The solvent that is used in the method of the present invention should dissolve all of the polymer, the silver salt and the phthalate compound and should be completely removed at the drying step after coated on a support or glass plate, etc. Examples of this solvent include alcohols of 1 to 4 carbon atoms, and tetrahydrofuran.

The solvent or solvents used to prepare the coating solution should not attack the supporting substrate. It is preferred to use a supporting substrate, which is microporous and thus exhibits an excellent permeability.

The facilitated transport membrane may also be produced by a method where the solution is coated on the glass plate without using the support, dried and then removed from the glass plate. In any case where the solution is coated on the support or on the glass plate, the thickness of the polymer film is typically several $\mu$m although it can vary if necessary.

Separation of olefin/paraffin using the polymer membrane produced by the above method is carried out at a temperature and pressure at which permeates can be present in a gas state. Separation of olefin/paraffin mixtures, which have low molecular weights and are gaseous at room temperature, can be carried out at room temperature as in cases of ethane/ethane, propane/propane, and 1-butene/butane mixtures. However, separation of olefin/paraffin mixtures, which have high molecular weights and thus are present as liquid at room temperature, is carried out at a temperature higher than the boiling point of the mixture by more than 10° C.

Separation of the olefin/paraffin mixture using the facilitated transport membrane is achieved by diffusion of gas mixture being introduced and transport of complexes formed between carriers and olefins being introduced. As a result, in view of such two effects, a pressure difference across the membrane (permeate pressure) is preferably in the range of 1 to 5 atm.

The present invention will hereinafter be described in further detail by examples. It should however be borne in mind that the present invention is not limited to or by the examples.

EXAMPLE 1

Two grams of polyvinylpyrrolidone (PVP, Mw=1,000,000) and 2 g of silver tetrafluoroborate (molar ratio of AgBF4/PVP=1) were successively dissolved in 8 g of methanol, after which 2 wt % of dibutylphthalate(0.04 g) with respect to PVP was added to the solution. The solution was coated on a support (microporous polysulfone membrane) was dried at room temperature in a light protected convection oven under a nitrogen atmos The resulting solid polymer membrane had a selective layer with a thickness of about 1 $\mu$m.

The produced membrane was cut into a size of 5 cm×5 cm and mounted in a permeance test apparatus. Permeance tests were then carried out for 100 hours at 2 atm with a gas mixture of propylene/propane (molar ratio=1:1).

Gas permeance were measured with a soap-bubble flowmeter, and separation properties of permeated gas were analyzed with a gas chromatograph equipped with TCD and Unibead-column.

The permeance and the propylene/propane selectivities were measured to be 54×10$^{-6}$ cm$^3$(STP)/cm$^2$·S·cmHg and 78 at one hour after the start of permeance test, and 51×10$^{-6}$ cm$^3$(STP)/cm$^2$·S·cmHg and 90 at 100 hours after the start of permeance test, respectively.

EXAMPLES 2–7

Polymer membranes were prepared as described in Example 1, using different loading of dibutylphthalate. Permeance tests were then carried out using the prepared polymer membranes. Results are shown in Table 1.

TABLE 1

| Examples | Dibutylphthalate/ polymer (wt %) | Permeance (10$^{-6}$ cm$^3$(STP)/ cm$^2$ · S · cmHg) | | Propylene/ propane selectivities | |
|---|---|---|---|---|---|
| | | 1 hour | 100 hours | 1 hour | 100 hours |
| 2 | 0.05 | 41 | 25 | 67 | 40 |
| 3 | 1 | 46 | 37 | 70 | 63 |
| 4 | 2.5 | 52 | 48 | 74 | 81 |
| 5 | 5 | 50 | 44 | 69 | 75 |
| 6 | 7 | 36 | 29 | 64 | 66 |
| 7 | 10 | 28 | 21 | 58 | 52 |

EXAMPLES 8–11

Polymer membranes were prepared as in Example 1 by using different silver salts. Permeance tests were then carried out using the prepared polymer membranes. Results are shown in Table 2.

TABLE 2

| Examples | Kinds of silver salt | Permeance (10$^{-6}$ cm$^3$(STP)/ cm$^2$ · S · cmHg) | | Propylene/propane selectivities | |
|---|---|---|---|---|---|
| | | 1 hour | 100 hours | 1 hour | 100 hours |
| 8 | AgSO$_3$CF$_3$ | 53 | 49 | 75 | 84 |
| 9 | AgPF$_6$ | 46 | 43 | 69 | 65 |
| 10 | AgClO$_4$ | 42 | 36 | 70 | 78 |
| 11 | AgSbF$_6$ | 39 | 36 | 81 | 89 |

EXAMPLES 12–14

Permeance tests were carried out using the polymer membrane prepared as in Example 1 while varying kinds of olefin/paraffin mixtures were used. Results are shown in Table 3. However, separation of 1-pentene/pentane mixtures in Example 14 was carried out at 50° C.

TABLE 3

| Examples | Gas mixtures | Permeance (10$^{-6}$ cm$^3$(STP)/ cm$^2$ · S · cmHg) | | Propylene/propane selectivities | |
|---|---|---|---|---|---|
| | | 1 hour | 100 hours | 1 hour | 100 hours |
| 12 | Ethane/ethane | 58 | 56 | 165 | 181 |
| 13 | 1-butene/butane | 49 | 45 | 77 | 85 |
| 14 | 1-pentene/pantane | 46 | 39 | 53 | 61 |

EXAMPLES 15–17

Polymer membranes were prepared as described in Example 1 while varying kinds of phthalates. Permeance tests were then carried out using the prepared membranes. Results are shown in Table 4.

TABLE 4

| Examples | Kinds of phthalates | Permeance ($10^{-6}$ cm³(STP)/ cm² · S · cmHg) 1 hour | 100 hours | Propylene/propane selectivities 1 hour | 100 hours |
|---|---|---|---|---|---|
| 15 | Dimethylphthalate | 45 | 42 | 75 | 84 |
| 16 | Dioctylphthalate | 49 | 47 | 108 | 123 |
| 17 | Diphenylphthalate | 59 | 56 | 119 | 130 |

EXAMPLES 18–22

Polymer membranes were similarly prepared as in Example 1 using different polymers. Permeance tests were then conducted using the prepared polymer membranes. Results are shown in Table 5.

TABLE 5

| Examples | Kinds of polymers | Permeance ($10^{-6}$ cm³(STP)/ cm² · S · cmHg) 1 hour | 100 hours | Propylene/propane selectivities 1 hour | 100 hours |
|---|---|---|---|---|---|
| 18 | Poly(2-ethyl-2-oxazoline) | 48 | 45 | 63 | 76 |
| 19 | Polyvinylmethylketone | 41 | 37 | 76 | 88 |
| 20 | Polyvinylformal | 42 | 40 | 74 | 85 |
| 21 | Polyvinylacetate | 47 | 42 | 61 | 75 |
| 22 | Polymethylmethacrylate (PMMA) | 45 | 41 | 63 | 72 |

EXAMPLES 23–24

Two grams of cellulose acetate (CA) (Example 23) or cellulose acetate butyrate (CAB) (Example 24) and 3.5 g of silver tetrafluoroborate were successively dissolved in 18 g of tetrahydrofuran (THF), to which 0.04 g of dibutylphthalate was then added to make a coating solution.

The solution was coated on a glass plate. After the evaporation of the solvent, the membranes were dried completely. Permeance tests were then carried out using the prepared polymer membranes. Results are shown in Table 6.

TABLE 6

| Examples | Kinds of polymers | Permeance ($10^{-6}$ cm³(STP)/ cm² · S · cmHg) 1 hour | 100 hours | Propylene/propane selectivities 1 hour | 100 hours |
|---|---|---|---|---|---|
| 23 | CA | 27 | 26 | 123 | 125 |
| 24 | CAB | 34 | 32 | 132 | 143 |

Comparative Examples 1–3

Polymer membranes were prepared as in Example 1 using only the polymers and the silver salts without adding phthalates. The molar ratios of silver salt and the repeating unit of polymer were set at 0.5, 1 and 2, respectively. Permeance tests were conducted using the prepared membranes. Results are shown in Table 7.

TABLE 7

| Comparative Examples | Molar ratios of silver salts to repeating units of polymers | Permeance ($10^{-6}$ cm³ (STP)/cm² · S · cmHg) 1 hour | 10 hours | 100 hours | Propylene/propane selectivities 1 hour | 10 hours | 100 hours |
|---|---|---|---|---|---|---|---|
| 1 | 0.5 | 18 | 14 | 10 | 42 | 40 | 29 |
| 2 | 1 | 40 | 29 | 25 | 65 | 61 | 35 |
| 3 | 2 | 60 | 40 | 37 | 59 | 53 | 26 |

In the separation membrane of Comparative Example 2 comprising only the polymer and the silver tetrafluoroborate (molar ratio of silver salt to the repeating unit of polymer was 1), the permeance continuously decreased up to 100 hrs. Thus, the permeance at 100 hrs was reduced to a level of 60% as compared to the permeance at 1 hr. Also, a propylene/propane selectivity was continuously reduced, and a selectivity at 100 hours was reduced to a level of about 50% as compared to a selectivity at 1 hour.

On the contrary, as in the case of Example 1 where a molar ratio of the silver salt to the repeating unit of the polymer was 1 and the phthalate loading was 2 wt. % with respect to the polymer, the permeance and selectivity remained substantially constant throughout the experiments for up to 100 hours.

As apparent from the foregoing, the present invention provides the facilitated transport membrane containing silver salt for olefin/paraffin separation having improved stability and also the method for producing thereof, which exhibits no deterioration in membrane performance. Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A method of preparing a facilitated transport membrane for olefin/paraffin separation comprising steps of:

successively dissolving a polymer, a silver salt and a phthalate compound, in a solvent, so as to form a homogeneous solution; and coating said solution onto a support substrate; and drying the coated support in a condition free from light and oxygen.

2. The method of claim 1, wherein said solvent is alcohol of 1 to 4 carbon atoms, or tetrahydrofuran (THF).

3. The method of claim 1, wherein said support substrate is microporous.

4. The method of claim 1, wherein said solution is coated onto a glass plate without using the support substrate, dried and then removed from the glass plate.

* * * * *